United States Patent [19]

Rossignol

[11] 4,315,018

[45] Feb. 9, 1982

[54] SPECIFIC PARASITICIDAL USE OF 2-BENZAMIDO-5-NITRO-THIAZOLE DERIVATIVES

[76] Inventor: Jean F. Rossignol, 16 Rue de Siam F-75016, Paris, France

[21] Appl. No.: 967,454

[22] Filed: Dec. 7, 1978

[51] Int. Cl.$^3$ .......................................... A61K 31/425
[52] U.S. Cl. ................................................... 424/270
[58] Field of Search ........................................ 424/270

[56] References Cited

U.S. PATENT DOCUMENTS 3,950,351  4/1976  Rossignol et al. .................. 424/270

*Primary Examiner*—Sam Rosen
*Attorney, Agent, or Firm*—Sughrue, Mion, Zinn, Macpeak & Seas

[57] ABSTRACT

The 2-benazmido-5-nitro-thiazole derivatives disclosed in U.S. Pat. No. 3,950,351 are effective against various species of cestodes: *Taenia pisiformis, Dypilidium caninum, Echinococus granulosus* and *Moniezia expansa,* and various species of nematodes: roundworms (Ancyslotoma spp.) and whipworms (Trichuris spp.).

33 Claims, No Drawings

SPECIFIC PARASITICIDAL USE OF 2-BENZAMIDO-5-NITRO-THIAZOLE DERIVATIVES

BACKGROUND OF THE INVENTION

In earlier U.S. Pat. No. 3,950,351, filed Aug. 8, 1974, issued Apr. 13, 1976, claiming priority of U.K. Application No. 37608/73, filed Aug. 8, 1973, there is disclosed derivatives of 2-benzamido-5-nitro-thiazole represented by the formula:

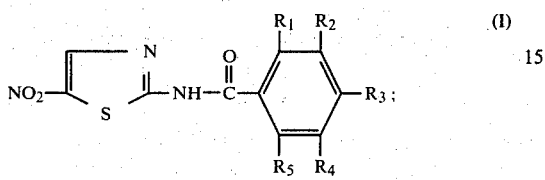

in which at least one of the symbols $R_1$, $R_2$, $R_3$, $R_4$ and $R_5$ represents an acyloxy group, preferably an acetoxy or propionoxy group, whereas the remaining symbols represent hydrogen or one of said remaining symbols represents an alkoxy group, such as the methoxy group, or a halogen atom, such as a chlorine or bromine atom, as interesting parasiticide, fungistatic and molluscidal agents.

The earlier patent also discloses a process for preparing the compounds as well as compositions containing at least one of the compounds as an active parasiticidal, fungistatic and/or molluscidal ingredient, together with a suitable pharmaceutical carrier.

In the earlier patent, the following specific compounds are disclosed.

TABLE 1

| Code Number | Substituents In Formula I | Melting Point °C. | Formula Weight | Mol. |
| --- | --- | --- | --- | --- |
| PH 5776 | $R_1=O-COCH_3$; $R_2=R_3=R_4=R_5=H$ | 202 | $C_{12}H_9N_3O_5S=$ | 307 |
| PH 6049 | $R_1=O-COC_2H_5$; $R_2=R_3=R_4=R_5=H$ | 157 | $C_{13}H_{11}N_3O_5S=$ | 321 |
| PH 6045 | $R_1=R_3=R_4=R_5=H$; $R_2=O-COCH_3$ | 193 | $C_{12}H_9N_3O_5S=$ | 307 |
| PH 6046 | $R_1=R_2=R_4=R_5=H$; $R_3=O-CO-CH_3$ | 244 | $C_{12}H_9N_3O_5S=$ | 307 |
| PH 6056 | $R_1=R_4=O-COCH_3$; $R_2=R_3=R_5=H$ | 240 | $C_{14}H_{11}N_3O_7S=$ | 365 |
| PH 6058 | $R_1=R_3=O-COCH_3$; $R_2=R_4=R_5=H$ | 165 | $C_{14}H_{11}N_3O_7S=$ | 365 |
| PH 6059 | $R_1=R_5H$; $R_2=R_4=OCH_3$; $R_3=O-COCH_3$ | 222 | $C_{14}H_{13}N_3O_7S=$ | 367 |
| PH 6057 | $R_1=O-COCH_3$, $R_2=R_3=R_5=H$; $R_4=Cl$ | 173 | $C_{12}H_8N_3O_5SCl=$ | 341.5 |
| PH 6103 | $R_1=O-COCH_3$; $R_2=R_3=R_5=H$; $R_4=Br$ | 187 | $C_{12}H_8N_3O_5SBr=$ | 386 |
| PH 6161 | $R_1=R_3=R_5=H$; $R_2=R_4=O-COCH_3$ | 211 | $C_{14}H_{11}N_3O_7S=$ | 365 |
| PH 6162 | $R_1=R_4=R_5=H$; $R_2=R_3=O-COCH_3$ | 206 | $C_{14}H_{11}N_3O_7S=$ | 365 |
| PH 6177 | $R_1=R_5=H$; $R_2=R_3=R_4=O-COCH_3$ | 243 | $C_{16}H_{13}N_3O_9S=$ | 423 |
| PH 6196 | $R_1=R_4=R_5=H$; $R_2=OCH_3$; $R_3=O-COCH_3$ | 236 | $C_{13}H_{11}N_3O_6S=$ | 337 |
| PH 6239 | $R_1=R_2=O-COCH_3$; $R_3=R_4=R_5=H$ | 191 | $C_{14}H_{11}O_7N_3S=$ | 393 |

A preferred disclosed compound is PH 5776.

In the earlier patent, parasiticidal activity is illustrated against Trichomonas, *Entamoeba dysenteriae*, *Syphacia obvelata*, *Hymenolepis nana* and *Biomphalaria glabrata*.

SUMMARY OF THE INVENTION

As is known to the skilled artisan, it is difficult, if not impossible, to predict effectiveness of chemical agents against specific parasites from activity against other parasites. This is particularly true in the area of nematodes and cestodes. Therefore, quite surprisingly, it has been found that compounds of the above formula (I), although described as having activity against *Hymenolepis nana* and *Syphacia obvelata*, are markedly effective against cestodes like *Taenia pisiformis, Dypilidium caninum, Echinococus granulosus* and *Moniezia expansa* and nematodes like *Ancylostoma* spp. and *Trichuris* spp.

Accordingly, it is an object of the present invention to provide chemical compounds useful in eradicating cestodes such as *Taenia pisiformis, Dypilidium caninum, Echinococus granulosus* and *Moniezia expansa* and nematodes such as roundworms and whipworms from animals infected therewith. More specifically, it is an object of the present invention to disclose processes for effectively treating animals infected with at least one of the above parasites by administering a parasiticidally effective amount of compound of the formula (I) to infected animals, usually as a single dose treatment.

DETAILED DESCRIPTION OF THE INVENTION

It has now been found that derivatives of 2-benzamido-5-nitro-thiazole represented by the following formula:

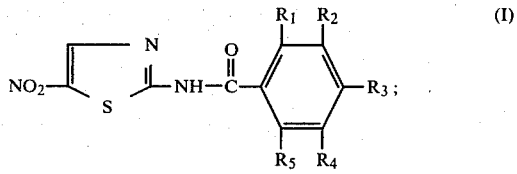

in which at least one of the symbols $R_1$, $R_2$, $R_3$, $R_4$ and $R_5$ represents an acyloxy group, whereas the remaining symbols represent hydrogen or one of said remaining symbols represents an alkoxy group or a halogen atom can be administered to warm-blooded animals infected with cestodes such as *Taenia pisiformis, Dypilidium caninum, Echinococus granulosus* and/or *Moniezia expansa* and nematodes such as *Ancylostoma* spp. and *Trichuris* spp. for effective eradication thereof.

As representative of the compounds of the formula (I), PH 5776, 2-(2'-acetoxy)-benzamido-5-nitro-thiazole was used in the following tests.

EXAMPLE I

Treatment Of *Taenia pisiformis* In Dogs

Fifteen beagles (8 male and 7 female), ranging in age from 8 to 30 months, were individually housed in stainless-steel cages and fed with commercial dog food. Water was provided ad libitum. After 2 weeks acclimatization, each dog was exposed to infection by administering orally 14–20 cysts containing *Taenia pisiformis* strobilocerci obtained 24 hours before from wild rabbits. Vitality of the cysts was verified by evagination in bile of the dog.

The dogs were divided in two groups, Groups 1 and 2, with respectively 7 and 8 animals.

The 15 dogs were fasted for 12 hours, and food was provided 3 hours after treatment.

The test material (PH 5776) was administered at a dosage of 75 mg/kg as a powder with 50% active ingredient.

Seven dogs (Group 1) were given the drug 6 weeks after infection with *Taenia pisiformis*, and the other 8 dogs (Group 2) were given the drug 8 weeks after infection.

Food and water intake, faecel consistency, vomiting, general appearance and behavior were recorded hourly during the day of treatment and twice daily thereafter.

For 2 days after medication, all faeces of each dog (Groups 1 and 2) were collected. The tapeworms that were found were then removed, counted and examined for scolices.

The emission time of the faeces for each dog was recorded during the day, when possible.

Nineteen days after treatment for Group 1, and 4 days after treatment for Group 2, the dogs were killed and the small intestines were examined in order to reveal the presence of Taenia spp. This 19-day waiting period for Group 1 allowed time for any viable scolices to redevelop, thus making them more easily visible at necropsy.

The intestines and intestinal contents from the pyloric portion of the stomach through the rectum were thoroughly examined for parasites.

Results

A certain quantity of tapeworm scolices with attached strobilae as well as free proglottids were collected in the faeces from the 8th to the 14th hour after the administration of medication. Tapeworm material was not found in the faeces collected after that time.

At necropsy, on the 19th day for Group 1, and on the 4th day for Group 2, after the administration of medication, tapeworms were not found in any of the 15 dogs.

Out of the 15 dogs, 11 (5 in Group 1, and 6 in Group 2) showed tapeworm material in the faeces. It could be considered as a normal rate of infection in an experimental study. Undesirable side effects of the treatment were not found in any of the 15 dogs.

The results of the test are tabulated in Table 2.

Conclusions

This experiment indicated that PH 5776 at a dosage of 75 mg of body weight was effective against *Taenia pisiformis*.

None of the dogs on study were positive for tapeworms at necropsy.

The object of treating 6- and 8-week old infection was to determine the effect of the drug on immature and mature *Taenia pisiformis*.

TABLE 2

| Group | Dog No. | Sex | Tapeworm Material In Faeces (8th–14th Hour) | Number Of Worms Recovered At Necropsy | Day of Sacrifice |
|---|---|---|---|---|---|
| 1 | N 01 | F | yes | 0 | On day 19 |
|   | N 04 | M | yes | 0 | |
|   | N 05 | F | no | 0 | |
|   | N 06 | M | yes | 0 | |
|   | N 10 | F | no | 0 | |

TABLE 2-continued

| Group | Dog No. | Sex | Tapeworm Material In Faeces (8th–14th Hour) | Number Of Worms Recovered At Necropsy | Day of Sacrifice |
|---|---|---|---|---|---|
|   | N 14 | M | yes | 0 | |
|   | N 15 | M | yes | 0 | |
| 2 | N 1 | F | yes | 0 | On day 4 |
|   | N 2 | F | no | 0 | |
|   | N 5 | F | yes | 0 | |
|   | N 7 | F | yes | 0 | |
|   | N 09 | M | yes | 0 | |
|   | N 18 | M | no | 0 | |
|   | M 9 | M | yes | 0 | |
|   | M 16 | M | yes | 0 | |

EXAMPLE 2

Treatment Of *Dypilidium caninum* In Dogs

Ten dogs, each having a naturally acquired infection, were treated at a dosage of 100 mg/kg using tablets containing 0.5 gram PH 5776. In general, the testing procedure was substantially the same as in Example 1 except necropsy 21 days after treatment. The treatment was 100% effective.

EXAMPLE 3

Treatment Of *Echinococus granulosus* In Dogs

Again, the general testing procedure was that of Example 1. This time 16 dogs to be treated were experimentally infected and divided into two groups along with 4 infected control dogs in each group. The 8 dogs of Group 1 were treated 4 weeks after infection, and the 8 dogs of Group 2 were treated 6 weeks after infection, each at a dose of 200 mg/kg, using the 0.5 gram active ingredient tablets. 100% efficacy of the single dose treatment was found upon necropsy 4 days after treatment.

EXAMPLE 4

Treatment Of *Moniezia Expansa* In Lambs

Experimental Design

Twenty lambs spontaneously infested by nematodes and cestodes were removed from a flock near Limoges (Haute-Vienne), France. They were housed in sheepfold —concentrate food, 1 kg per day per lamb, water and hay, ad libitum, were provided.

To confirm the infestation, faeces were taken from the rectum 48 hours prior to treatment and the number of eggs counted.

The animals were assigned to treatment groups as indicated below:

| Group | Number Of Animals | Treatment |
|---|---|---|
| 1 | 7 | 100 mg/kg PH 5776 |
| 2 | 7 | 50 mg/kg PH 5776 |
| 3 | 6 | Control (water + gum syrup) |

Seven lambs (Group 1, black) were given a single 100 mg/kg of body weight dose of the test material dissolved in a mixture of water and gum syrup (0.5 ml/kg of body weight) orally administered with a syringe.

Seven lambs (Group 2, red) were given a single 50 mg/kg of body weight dose of the test material dissolved in a mixture of water and gum syrup (0.5 ml/kg of body weight) orally administered with a syringe.

Six lambs (Group 3, blue) were given 0.5 ml/kg of body weight of a mixture of water and gum syrup orally administered with a syringe.

Results 48 hours after treatment, necroscopies were performed. No changes in the internal organs and no coloration of the tissues were observed. Nevertheless, the tissues of the small intestine wall were slightly colored yellow in the treated groups.

Scolices and gastro intestinal worm counts were carried out.

Data reported in Table 3 suggest the following comments:

Group 1, Black, 100 mg/kg, PH 5776

48 hours before treatment, the faeces examinations show a constant infestation by Moniezia spp. in the 7 animals.

48 hours after treatment, lamb (number 6) was still positive with 2 scolices found. It, however, has to be emphasized that the content of the rumen of the same animal was found at necroscopy to be highly colored yellow. This may well suggest that the major or entire part of the dose was ingested into the rumen instead of reaching the abomasum via the oesophagus.

Group 2, Red, 50 mg/kg, PH 5776

48 hours before treatment, no faeces could be taken from 2 lambs (numbers 5 and 7); 5 others are positive for Moniezia spp. at faecal examination.

At necroscopy, 48 hours after treatment, 3 lambs (numbers 1, 4 and 5) are still infested with the cestoda (1 scolex found in each intestine).

Again, the content of one rumen (number 5, red) was found to be highly colored yellow, suggesting the same comments as for the case previously described (number 6, red).

It is pointed out that the lamb number 7 could not be sampled before treatment. The negative result recorded at necroscopy cannot, therefore, be fully attributed to the drug activity.

Group 3, Blue, Control 48 hours before treatment, feacal examination shows:
1 negative result for Moniezia spp. (number 4);
no faeces in one animal (number 5); and
4 positive results for Moniezia spp. (numbers 1, 2, 3 and 6).

At necroscopy, 5 out of 6 lambs were positive, the number of scolices ranging from 0 to 10 (when scolices were not present, the presence of segments of parasites were used to establish if the animal was positive or not).

The negative count at necroscopy (number 6) was positive at feacal examination. As this lamb did not receive any treatment, it is suggested the clearance could be attributed to a self-cure phenomenon.

Gastro Intestinal Nematodes 48 hours before treatment, coprological control indicates a constant infestation in the 3 groups (20 lambs) with these parasites.

48 hours after treatment, data reported in Table 4 suggest that the test material PH 5776 has no toxic effect on any of the present round worms (Ostertagia, Hoemonchus, T-axei, Hematodirus, Cooperia, Trichostrongylus spp., Chabertia, Oesophagostormum).

Conclusions

PH 5776 at a single dose of 100 mg/kg of body weight appears to be very active against Moniezia spp. (almost 100%) as it could be shown on a lot of 7 naturally infested lambs.

At half of this posology (50 mg/kg), the efficacy is decreasing. However, the total number of scolices recovered is less in that lot than in the control group; only 3 lambs were negative after treatment.

The compound does not reveal any efficacy in the test treatment of gastro-intestinal nematode infestation of the lambs.

TABLE 3

| | | | | RESULTS (cestoda) Moniezia spp. | | | |
| | | | | Before Treatment Faeces | After Treatment | | |
| Group | Number | Treatment | Weight (kg) | Examination (Egg Count) | Result | Number Of Scolex | Observation |
|---|---|---|---|---|---|---|---|
| 1 | 1. (black) | PH 5776 | 18 | + | − | 0 | |
| | 2. (black) | 100 mg/kg | 22 | + | − | 0 | |
| | 3. (black) | | 23 | ++ | − | 0 | |
| | 4. (black) | | 27 | + | − | 0 | |
| | 5. (black) | | 25 | + | − | 0 | |
| | 6. (black) | | 21.5 | ++ | + | 2 | Rumen Colored Yellow |
| | 7. (black) | | 25 | + | − | 0 | |
| 2 | 1. (red) | PH 5776 | 24 | + | + | 1 | |
| | 2. (red) | 50 mg/kg | 21 | + | − | 0 | |
| | 3. (red) | | 26 | ++ | − | 0 | |
| | 4. (red) | | 16 | ++ | + | 1 | |
| | 5. (red) | | 22 | No Faeces | + | 1 | Rumen Colored Yellow |
| | 6. (red) | | 19 | ++ | − | 0 | |
| | 7. (red) | | 23 | No Faeces | − | 0 | |
| 3 | 1. (blue) | Controls | 20 | ++ | + | 7 | |
| | 2. (blue) | | 22 | + | + | 3 | |
| | 3. (blue) | | 17 | + | + | No Scolex But Segments | |
| | 4. (blue) | | 26 | No Egg | + | 4 | |
| | 5. (blue) | | 22 | No Faeces | + | 10 | |

TABLE 3-continued

RESULTS (cestoda)
Moniezia spp.

| Group | Number | Treatment | Weight (kg) | Before Treatment Faeces Examination (Egg Count) | After Treatment Result | Number Of Scolex | Observation |
|---|---|---|---|---|---|---|---|
| | 6. (blue) | | 17 | ++ | — | 0 | |

TABLE 4

RESULTS
Gastro-Intestinal Nematodes

| Group | Number | Treatment | Before Treatment Number Of Worms (Egg Count) | Number Of Worms Abomasum | Number Of Worms Small Intestine | Number Of Worms Large Intestine | Number Of Worms Total |
|---|---|---|---|---|---|---|---|
| 3 | 1 | Controls | 500 | 3855 | 1840 | 10 | 5705 |
| | 2 | | 1550 | 4179 | 940 | 10 | 5129 |
| | 3 | | 30 | 744 | 30 | 0 | 774 |
| | 4 | | 2800 | 2859 | 1580 | 0 | 4439 |
| | 5 | | No Faeces | 1308 | 360 | 30 | 1698 |
| | 6 | | 350 | 1880 | 880 | 0 | 2760 |
| 2 | 1 | PH 5776 | 400 | 863 | 1440 | 0 | 2303 |
| | 2 | 50 mg/kg | 2100 | 8743 | 1500 | 0 | 10243 |
| | 3 | | 30 | 1863 | 1420 | 0 | 3283 |
| | 4 | | 1050 | 2608 | 1120 | 0 | 3728 |
| | 5 | | No Faeces | 13326 | 3250 | 20 | 5596 |
| | 6 | | 1050 | 2961 | 1825 | 0 | 4786 |
| | 7 | | No Faeces | 3164 | 1380 | 0 | 4544 |
| 1 | 1. | PH 5776 | 60 | 5561 | 170 | 0 | 5731 |
| | 2 | 100 mg/kg | 750 | 1605 | 650 | 0 | 2255 |
| | 3 | | 45 | 1427 | 1610 | 0 | 3037 |
| | 4 | | 1350 | 4977 | 1180 | 0 | 6157 |
| | 5 | | 100 | 1812 | 2900 | 0 | 4712 |
| | 6 | | 300 | 705 | 450 | 0 | 1155 |
| | 7 | | 1100 | 1222 | 130 | 0 | 1355 |

EXAMPLE 5

Treatment of Nematodes In Dogs

Although PH 5776 has no activity against gastro-intestinal nematodes in sheep, activity against other species of nematodes has been found in dogs.

The general testing procedure was that of Example 1. This time 3 dogs, each having a naturally acquired infection, were treated at a dosage of 100 mg/kg using tablets containing 0.5 g PH 5776. 100% efficacy against whipworms and 65% efficacy against hookworms were found upon necropsy 4 days after treatment using a single dose treatment.

In another trial, 3 repeated doses at an interval of 7 days of 100 mg/kg showed 93% efficacy against an infection of the hookworms in dogs.

Toxicity data on compound PH 5776 on mice is given in U.S. Pat. No. 3,950,351.

Additional toxicity studies have been carried out in cats and dogs, which can be summarized as follows.

The lethal dose of the test material in cats is greater than 10 g/kg. Minimal signs (slight diarrhea) of intoxication were observed after single doses of 1 g/kg of the test material. At doses of 5 and 10 g/kg, there was a suggestion of central nervous system depression. Necropsy findings consisting of a slight yellow discoloration of the renal cortex suggested the urine as a route of excretion.

The lethal dose of the test material in dogs is greater than 10 g/kg. Minimal signs of intoxication related to gastro-intestinal distress were observed after single doses of 1, 5 or 10 g/kg of the test material.

From the above data, dosage will be at a level of about 50–200 mg/kg, given as a single dose. As is apparent, dosage will vary somewhat depending upon suspected parasite.

What is claimed is:

1. A process for treating a dog or cat infected with Taenia which comprises administering to the infected animal an eradicating effective amount of a compound of the formula:

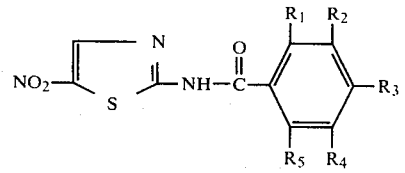

in which one or two of the symbols $R_1$, $R_2$, $R_3$, $R_4$ and $R_5$ represents an acetoxy or propionyloxy group, and the remaining symbols represent hydrogen with the proviso that one of the remaining symbols can represent a methoxy group or a chlorine or bromine atom.

2. The process of claim 1 wherein a single dose of the compound is administered.

3. The process of claim 2 wherein the dose is 50–200 mg/kg.

4. The process of claim 1 wherein the compound is 2-(2'-acetoxy)-benzamido-5-nitro-thiazole.

5. The process of claim 1 wherein the compound is 2-(2'-propionyloxy)-benzamido-5-nitro-thiazole.

6. A process for treating a dog or cat infected with Dypilidium which comprises administering to the infected animal an eradicating effective amount of a compound of the formula:

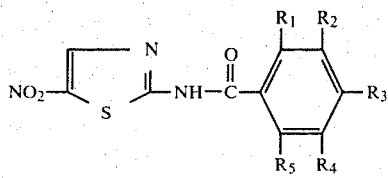

in which one or two of the symbols $R_1$, $R_2$, $R_3$, $R_4$ and $R_5$ represents an acetoxy or propionyloxy group, and the remaining symbols represent hydrogen with the proviso that one of the remaining symbols can represent a methoxy group or a chlorine or bromine atom.

7. The process of claim 6 wherein a single dose of the compound is administered.

8. The process of claim 7 wherein the dose is 50-200 mg/kg.

9. The process of claim 6 wherein the compound is 2-(2'-acetoxy)-benzamido-5-nitro-thiazole.

10. The process of claim 6 wherein the compound is 2-(2'-propionyloxy)-benzamido-5-nitro-thiazole.

11. A process for treating a dog or cat infected with Echinococcus spp. which comprises administering to the infected animal an eradicating effective amount of a compound of the formula:

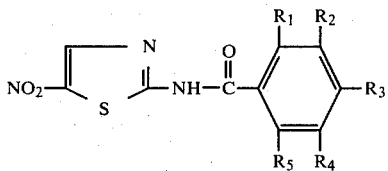

in which one or two of the symbols $R_1$, $R_2$, $R_3$, $R_4$ and $R_5$ represents an acetoxy or propionyloxy group, and the remaining symbols represent hydrogen with the proviso that one of the remaining symbols can represent a methoxy group or a chlorine or bromine atom.

12. The process of claim 11 wherein a single dose of the compound is administered.

13. The process of claim 12 wherein the dose is 50-200 mg/kg.

14. The process of claim 11 wherein the compound is 2-(2'-acetoxy)-benzamido-5-nitro-thiazole.

15. The process of claim 11 wherein the compound is 2-(2'-propionyloxy)-benzamido-5-nitro-thiazole.

16. A process for treating sheep infected with *Moniezia expansia* which comprises administering to the infected animal an eradicating effective amount of a compound of the formula:

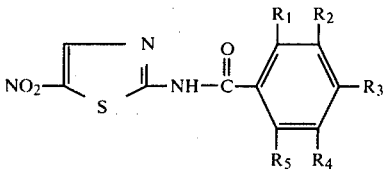

in which one or two of the symbols $R_1$, $R_2$, $R_3$, $R_4$ and $R_5$ represents an acetoxy or propionyloxy group, and the remaining symbols represent hydrogen with the proviso that one of the remaining symbols can represent a methoxy group or a chlorine or bromine atom.

17. The process of claim 16 wherein a single dose of the compound is administered.

18. The process of claim 17 wherein the dose is 50-200 mg/kg.

19. The process of claim 16 wherein the compound is 2-(2'-acetoxy)-benzamido-5-nitro-thiazole.

20. The process of claim 10 wherein the compound is 2-(2'-propionyloxy)-benzamido-5-nitro-thiazole.

21. A process for treating a dog or cat infected with Ancylostoma spp. which comprises administering to the infected animal an eradicating effective amount of a compound of the formula:

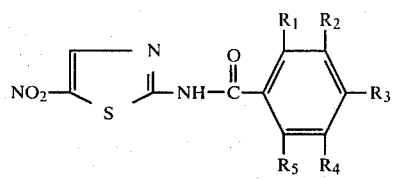

in which one or two of the symbols $R_1$, $R_2$, $R_3$, $R_4$ and $R_5$ represents an acetoxy or propionyloxy group, and the remaining symbols represent hydrogen with the proviso that one of the remaining symbols can represent a methoxy group or a chlorine or bromine atom.

22. The process of claim 21 wherein a single dose of the compound is administered.

23. The process of claim 22 wherein the dose is 50-200 mg/kg.

24. The process of claim 21 wherein the compound is 2-(2'-acetoxy)-benzamido-5-nitro-thiazole.

25. The process of claim 21 wherein the compound is 2-(2'-propionyloxy)-benzamido-5-nitro-thiazole.

26. The process of claim 21 wherein a single dose of 50 mg/kg is employed.

27. A process for treating a dog or cat infected with Trichuris spp. which comprises administering to the infected animal an eradicating effective amount of a compound of the formula:

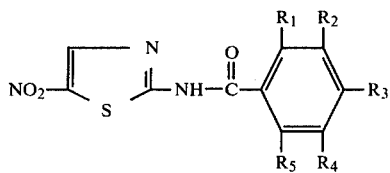

in which one or two of the symbols $R_1$, $R_2$, $R_3$, $R_4$ and $R_5$ represents an acetoxy or propionyloxy group, and the remaining symbols represent hydrogen with the proviso that one of the remaining symbols can represent a methoxy group or a chlorine or bromine atom.

28. The process of claim 27 wherein a single dose of the compound is administered.

29. The process of claim 27 wherein multiple doses are employed.

30. The process of claim 29 wherein the dose is 50-200 mg/kg.

31. The process of claim 27 wherein the compound is 2-(2'-acetoxy)-benzamido-5-nitro-thiazole.

32. The process of claim 27 wherein the compound is 2-(2'-propionyloxy)-benzamido-5-nitro-thiazole.

33. The process of claim 29 wherein 3 doses of about 100 mg/kg are employed.

* * * * *